United States Patent [19]

Bomann et al.

[11] Patent Number: 4,853,402

[45] Date of Patent: Aug. 1, 1989

[54] FEED ADDITIVE FOR IMPROVING GROWTH IN AGRICULTURAL ANIMALS

[75] Inventors: Werner Bomann; Franz Esser; Ulrich Hamel; Helmut Stäble, all of Ingelheim am Rhein, Fed. Rep. of Germany

[73] Assignee: Boehringer Ingelheim Vetmedica GmbH, Ingelheim am Rhein, Fed. Rep. of Germany

[21] Appl. No.: 19,447

[22] Filed: Feb. 26, 1987

Related U.S. Application Data

[63] Continuation of Ser. No. 760,239, Jul. 30, 1985, abandoned.

[30] Foreign Application Priority Data

Aug. 1, 1984 [DE] Fed. Rep. of Germany ....... 3428342

[51] Int. Cl.$^4$ .......................................... A61K 31/415
[52] U.S. Cl. .................................... 514/401; 514/392; 514/402; 514/256; 514/261; 514/245; 514/246; 514/215; 514/617; 514/632; 514/634; 514/227.2; 514/383; 514/368; 514/396; 514/387; 514/363; 514/657; 514/653; 514/605
[58] Field of Search .................................. 514/401, 392

[56] References Cited

FOREIGN PATENT DOCUMENTS 2096987 10/1982 United Kingdom ................ 514/401

*Primary Examiner*—Frederick E. Waddell
*Attorney, Agent, or Firm*—David E. Frankhouser; Alan R. Stempel

[57] ABSTRACT

By using α-mimetics, particularly compounds of general formulae I to III and the compounds listed in Table I, as feed additives in fattening animals, it has surprisingly been possible to improve the daily weight gain, the utilisation of fodder and the ratio of muscle to fat in favor of the proportion of muscle and protein.

3 Claims, No Drawings

FEED ADDITIVE FOR IMPROVING GROWTH IN AGRICULTURAL ANIMALS

This is a continuation of application Ser. No. 760,239, filed July 30, 1985, now abandoned.

FIELD OF THE INVENTION

The invention relates to feed additives for improving growth in agricultural animals.

BACKGROUND OF THE INVENTION

Sympathomimetics impart their effects via α and β receptors. Of the sympathomimetics, there are natural and synthetic substances which are predominantly effective either via β or via α receptors.

The activity of sympathomimetics which act predominantly via α receptors consists, for example, in the contraction of the smooth muscle of the blood vessels and uterus, the sphincters in the gastrointestinal tract and the M. dilatator Pupillae (mydriasis). They also have a relaxant effect on the longitudinal muscle of the gastrointestinal tract and cause glycogenolysis in the liver.

The α-mimetics are known to be useful systemically for producing hypotensive regulation of the circulation, and locally for reducing inflammation of the mucous membranes in the nose, for stopping diffuse bleeding, as a mydriatic and as an additive to local anaesthetics.

It is known that in some species of laboratory animals, intravenous administration of clonidine results in a brief (limited to a few hours) but substantial increase in the production of growth hormones and that intramuscular administration in monkeys leads to an increase in appetite and a consequent increase in food intake and a brief weight gain. The food intake in rats has also been shown to increase after intracerebral administration of this drug.

SUMMARY OF THE INVENTION

It has now been found that α-mimetics are useful as additives in feed for agricultural animals. Animals raised on feed containing α-mimetic additives exhibit increased weight gain and utilize fodder more efficiently than is the case with regular feed.

In particular, those α-mimetic imidazolines of formula I, imido[1,2-a]s-triazines of formula II, azepines of formula III, as described fully herein, the compounds listed in the following Table I, as well as the physiologically acceptable acid addition salts thereof, are especially useful as feed additives in accordance with the invention.

DETAILED DESCRIPTION OF THE INVENTION

The imidazolines useful as feed additives according to the invention are of the formula

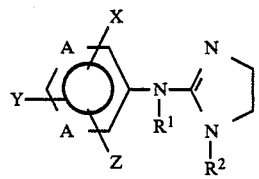

wherein:

$R^1$ is hydrogen, alkyl or tetrahydropyran;

$R^2$ is hydrogen, benzoyl or acetonyl;

A is carbon or nitrogen;

Y is hydrogen, a halogen atom, such as, for example, F, Cl or Br, alkyl, haloalkyl, alkoxy, haloalkoxy, amino, nitro, hydroxy, alkylthio, halothio, or cyclopropyl; and, X and Z are the same or different and each is hydrogen, a halogen atom, such as, for example, F, Cl or Br, alkyl, haloalkyl, alkoxy, haloalkoxy, amino, nitro, hydroxy, alkylthio, or halothio; or, X and Z together form

=N—S—N=,

—N=(CH$_2$)=N—,

=N—N(CH$_3$)—CH=, or

—(CH$_2$)$_4$—.

The imidazo[1,2-a]s-triazines useful as feed additives are those of the formula

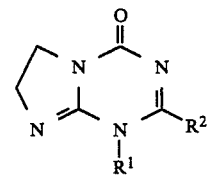

wherein:

$R^1$ is unsubstituted phenyl or phenyl which is mono-, di-, or tri-substituted by halogen atoms, preferably fluorine, chlorine or bromine atoms, methyl, methoxy, or trifluoromethyl, the substituents on said phenyl being the same or different; and, $R^2$ is hydrogen, phenyl, or phenyl which is mono- or poly-substituted by halogen atoms, preferably chlorine atoms.

The azepine derivatives useful as feed additives are those of the formula

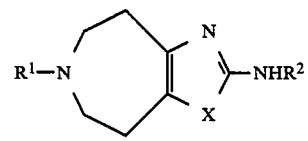

wherein:

$R^1$ is hydrogen, straight-chained or branched $C_{1-4}$ alkyl which may optionally be substituted by hydroxyl, allyl, cycloalkyl, hexahydrobenzyl, phenyl, phenylethyl or benzyl, wherein such benzyl group may be substituted in the nucleus by one or two halogen atoms, by one to three methoxy groups, by a trifluoromethyl group or $C_{1-3}$ alkyl and, if X is sulphur, then $R^2$ is hydrogen, straight-chained or branched $C_{1-5}$ alkyl, allyl, cycloalkyl, phenyl, benzyl or phenylethyl or, if X is oxygen, then $R^2$ is hydrogen.

Further compounds useful as feed additives are given in the following table.

TABLE 1

(1) 2-[1-(2,6-Dichlorophenoxy)ethyl]-2-imidazoline

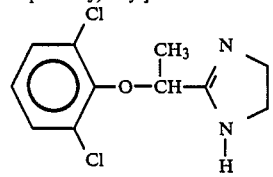

TABLE 1-continued (2) 2-[(2-Chloro-4-methyl-3-thienyl)amino]-2-imidazoline
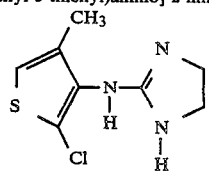

(3) 2,6-Dichlorophenylacetylguanidine
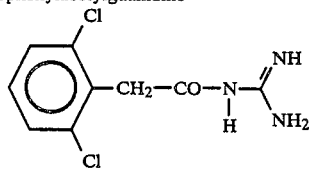

(4) 1-(2,6-Dichlorobenzylideneamino)guanidine
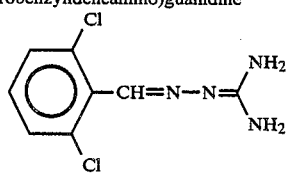

(5) 2-(2,6-Dimethylbenzylamino)-4,5-dihydro-6H—1,3-thiazine
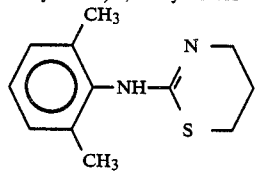

(6) 2,6-Dichlorobenzaldehyde-(4-amino-4H—1,2,4-triazol-3-yl)-hydrazone
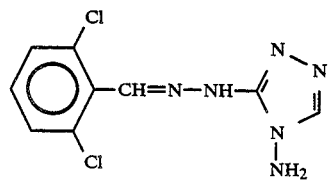

(7) 2-(2,6-Dichlorophenyl)-5,6-dihydroimidazo-[2,1-b]-thiazole
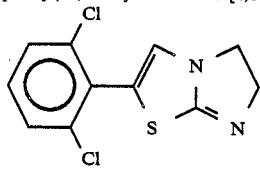

(8) 4-(2,6-Dimethylbenzyl)imidazole,
1-(Imidazol-4-yl)-2-(2,6-dimethylphenyl)-ethane,
1-(Imidazol-4-yl)-3-(2,6-dimethylphenyl)-propane,
1-(Imidazol-4-yl)-4-(2,6-dimethylphenyl)-butane
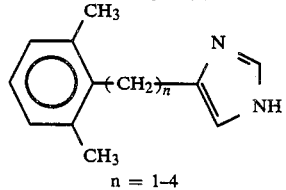
n = 1-4

(9) 6-(2,6-Dichlorophenyl)-2,3,6,7-tetrahydro-5H—pyrrolo[2,1-b]imidazole,
6-(2-Chloro-6-fluorophenyl)-2,3,6,7-tetrahydro-5H—pyrrolo[2,1-b]imidazole,
6-(2,6-Dichloro-3-methylphenyl)-2,3,6,7-tetrahydro- TABLE 1-continued 5H—pyrrolo[2,1-b]imidazole
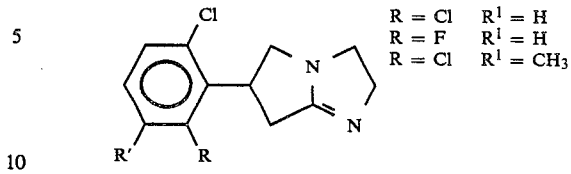
R = Cl   R¹ = H
R = F    R¹ = H
R = Cl   R¹ = CH₃

(10) 2-(4-t-Butyl-2,6-dimethyl-3-hydroxy-benzyl)-2-imidazoline
2-(4-t-Butyl-2,6-dimethyl-benzyl)-2-imidazoline
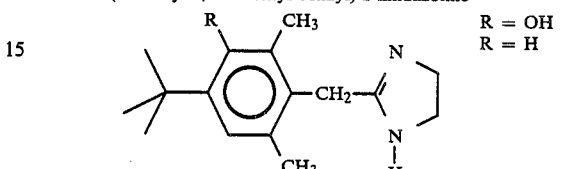
R = OH
R = H

(11) 2-(1,2,3,4-Tetrahydro-1-naphthyl)-2-imidazoline
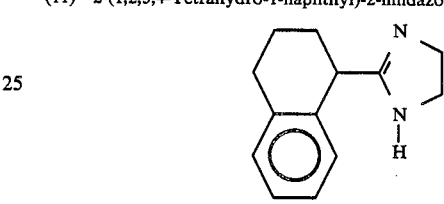

(12) 2-(1-40-Naphthylmethyl)-2-imidazoline
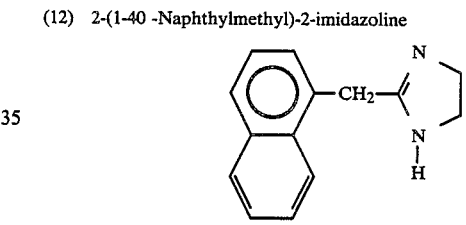

(13) 2-(2-Methoxy-5-chlorophenyl)azoimidazole
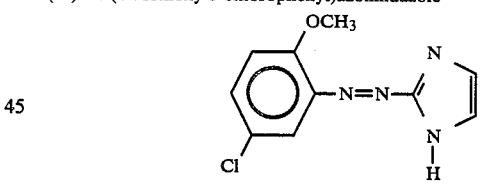

(14) 2-[N—(4-Hydroxy-2-methylbenzylidene)hydrazino]-2-imidazoline
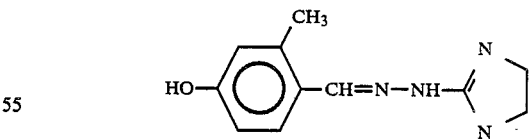

(15) 2-Dimethylamino-5,6-dihydroxy-1,2,3,4-tetrahydro-naphthalene
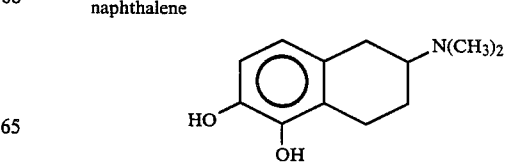

(16) 5-Chloro-4-(2-imidazolin-2-ylamino)-2,1,3-benzothiadiazole

TABLE 1-continued

(17) 4-(2-Imidazolin-2-ylamino)-2-methyl-benzopyrazole

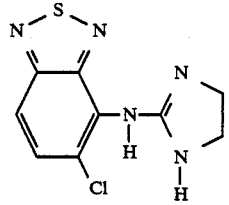

(18) 2-Amino-1-(2,5-dimethoxyphenyl)-propanol

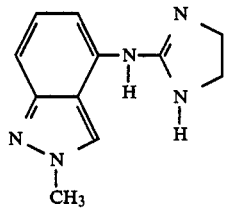

(19) 1-(3-Hydroxyphenyl)-2-methylamino-ethanol

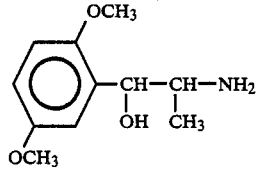

(20) 2-[(O—Cyclopropylphenoxy)methyl]-2-imidazoline

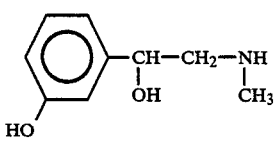

(21) 3'-(1-Hydroxy-2-methylaminoethyl)methanesulphoanilide

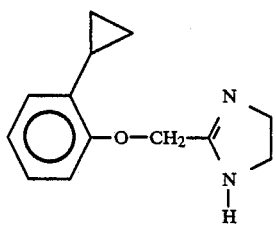

(22) 2-Amino-5-methylthio-8-methoxy-1,2,3,4-tetrahydro-naphthalene

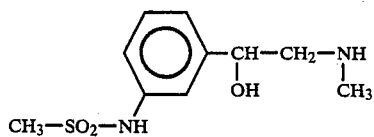

Of the group of formulae I–III the following compounds are preferred:

(1) 2-(2,6-dichloroanilino)-2-imidazoline;
(2) 8-(2,6-dichlorophenyl)-7-(4-chlorophenyl)-5-oxo-2,3-dihydro-imidazo[1,2-a]s-triazine;
(3) 1-acetonyl-2(2,6-dichlorophenylamino)-2-imidazoline;
(4) 2-(2-bromo-6-fluoroanilino)-2-imidazoline;
(5) 2-(2-fluoro-6-trifluoromethylphenylamino)-2-imidazoline;
(6) 2-(2-chloro-5-trifluoromethylphenylamino)-2-imidazoline;
(7) 2-(2-chloro-4-cyclopropylphenylamino)-2-imidazoline;
(8) 2-(3-fluoro-4-methylphenylamino)-2-imidazoline;
(9) 2-(6-chloro-4-methoxy-2-methyl-pyrimidin-5-yl-amino)-2-imidazoline;
(10) 1-benzoyl-2-(2,6-dichloroanilino)-2-imidazoline;
(11) 2-[N-(2,6-dichlorophenyl)-N-tetrahydropyran-2-yl)amino]-2-imidazoline;
(12) 5-chloro-4-(2-imidazolin-2-yl-amino)-2,1,3-benzothiadiazole;
(13) 2-(1,2,3,4-tetrahydro-5-naphthylamino)-2-imidazoline;
(14) 2-(4-amino-2,6-dichlorophenylamino)-2-imidazoline;
(15) 4-(2-imidazolin-2-yl-amino)-2-methyl-1,2-benzopyrazole;
(16) 2-(3,4-dihydroxy-phenylamino)-2-imidazoline;
(17) 2-amino-6-ethyl-4,5,7,8-tetrahydro-6H-oxazolo[5,4-d]azepine;
(18) 2-amino-6-(p-chlorobenzyl)-4,5,7,8-tetrahydro-6H-thiazolo[5,4-d]azepine;
(19) 2-(4-bromo-quinoxalin-5-yl-amino)-2-imidazoline;

The foregoing compounds of formulae I–III and those listed in Table I are either known per se or can be readily synthesized.

It has been unexpectedly found that animals fed with feed comprising α-mimetics in accordance with the invention, particularly the α-mimetics of formulae I–III and the compounds listed in Table I, exhibit improved weight gain, even where food intake is reduced. Further, slaughter yields are increased and the carcasses are improved inasmuch as the ratio of muscle to fat is increased. There is no detrimental effect on the quality of the meat.

These effects in agricultural animals are achieved by daily administration through the fodder or by parenteral systems with delayed release of the active substance.

One particularly surprising feature is the fact that the improved performances observed can be maintained over fairly long periods of time, something which could not have been predicted on the basis of the endocrinal counter-regulatory measures to be expected.

Thus, the activites described above can remain fully effective throughout the periods of fattening or performance typical for each species of animal.

α-Mimetics thus constitute a valuable aid in animal production.

For this purpose, according to the invention, a compound as described hereinbefore is added in a concentration of from 0.02–20 ppm (pigs), 0.08–80 ppm (poultry) and 0.02–200 ppm (cattle) to the sole fodder, so as to achieve a daily dosage of from 1–1000 mcg/kg of body weight.

Examples of animals which would be considered include pigs, cattle, poultry for fattening, other poultry such as hens, ducks, geese or turkeys, sheep, rabbits and fish.

Examples of particularly suitable fodder which might contain one of the above compounds or a physiologically acceptable acid addition salt thereof in the concentrations specified above would include:

for pigs: milk replacement fodder for piglets, sole fodder for piglets (piglet rearing fodder), sole fodder I for fattening pigs up to about 50 kg, sole fodder II for fattening pigs of about 50 kg upwards, sole fodder for fattening pigs of about 35 kg upwards;

food supplements for piglets, food supplements I for fattening pigs, food supplement II for fattening pigs, high-protein food supplement for pigs or protein concentrate for pigs (food supplement), and for cattle milk replacement fodder for rearing calves, food supplement to be added to skimmed milk for rearing calves, food supplement for rearing calves, skimmed milk replacement fodder I for fattening calves, milk replacement fodder II for fattening calves of about 80 kg upwards, high-energy food supplement to be added to skimmed milk for fattening calves, food supplement for fattening cattle or high-protein food supplement for fattening cattle;

for sheep: milk replacement fodder for lambs or sole fodder for fattening lambs;

for poultry: sole fodder for fattening geese, food supplement for fattening geese, sole fodder for ducks, sole fodder for ducklings, sole fodder for hens in the first weeks of their lives, sole fodder for hens, sole fodder for young hens, sole fodder I for broilers, sole fodder II for broilers from about the fifth week of their life onwards, food supplement for hens, sole fodder for turkeys, sole fodder for turkey chicks or sole fodder for fattening hens;

for rabbits: sole fodder for fattening rabbits or food supplement for fattening rabbits; and, for fish: sole fodder for carp or sole fodder for trout or corresponding additional feed or supplementary feed.

Thus, for example, the concentration of one of the above compounds or a physiologically acceptable acid addition salt thereof is from 0.02 to 200 ppm in sole fodders and from 0.2 to 1000 ppm in food supplements.

The feed additive according to the invention differs from the antibacterial substances used hitherto which improve performance by affecting the flora of the intestines in that it directly influences the endocrine regulating systems which are involved in the growth process, so as to favour anabolic metabolism.

Moreover, it has a minor problem of residue, i.e. low toxicity, no inhibiting effect on bacterial growth and thus no dysbiosis and no formation or transmission of resistance.

The feed additive according to the invention differs from the feed additives known hitherto, in particular, by its preferred effect on improving the quality of the carcass, i.e. a selective improvement in the ratio of muscle to fat in favour of the proportion of muscle and protein.

The following Examples of feed compositions are intended to illustrate the invention (All the quantities given relate to percent by weight unless otherwise stated):

EXAMPLE 1

Sole fodder I for fattening pigs up to about 50 kg

|     |                                      |      |              |
| --- | ------------------------------------ | ---- | ------------ |
| (a) | Crude protein                        | min. | 16           |
|     | Lysine                               | min. | 0.8          |
|     | Crude fat                            | max. | 8            |
|     | Crude fibre                          | max. | 6            |
|     | Starch                               | min. | 33           |
|     | Calcium                              | min. | 0.7          |
|     | Phosphorus                           | min. | 0.5          |
|     | Sodium                               | min. | 0.15         |
| (b) | Copper                               | min. | 20 mg        |
|     | Zinc                                 | min. | 50 mg        |
|     | Vitamin A                            | min. | 4 000 IU     |
|     | Vitamin D                            | min. | 500 IU       |
| (c) | 2-(2,6-Dichloroanilino)-2-imidazoline | | 0.02–20 ppm |

EXAMPLE 2

Milk replacement fodder II for fattening calves of about 80 kg upwards (sole fodder)

|     |                                      |      |              |
| --- | ------------------------------------ | ---- | ------------ |
| (a) | Crude protein                        | min. | 17           |
|     | Lysine                               | min. | 1.25         |
|     | Crude fat                            |      | 15 to 30     |
|     | Crude fibre                          | max. | 2            |
|     | Crude ash                            | max. | 10           |
|     | Calcium                              | min. | 0.9          |
|     | Phosphorus                           | min. | 0.7          |
|     | Sodium                               | min. | 0.2          |
|     | Magnesium                            | min. | 0.13         |
|     | Powdered milk                        | min. | 25           |
| (b) | Copper                               | max. | 15 mg        |
|     | Vitamin A                            | min. | 8 000 IU     |
|     | Vitamin D                            | min. | 1 000 IU     |
|     | Vitamin E                            | min. | 20 mg        |
| (c) | 2-(2,6-Dichloroanilino)-2-imidazoline | | 0.02–200 ppm |

EXAMPLE 3

Cattle fattening fodder II (high-protein food supplement for fattening cattle)

|     |                                      |      |              |
| --- | ------------------------------------ | ---- | ------------ |
| (a) | Crude protein including:             |      | 30 to 40     |
|     | Crude protein from NPN compounds     | max. | 10           |
|     | Crude fat                            | max. | 10           |
|     | Crude fibre                          | max. | 12           |
|     | Crude ash                            | max. | 12           |
|     | Calcium                              |      | 1.6 to 2.4   |
| (b) | 2-(2,6-Dichloroanilino)-2-imidazoline | | 0.02–200 ppm |

EXAMPLE 4

Sole fodder I for broilers

|     |                                      |      |              |
| --- | ------------------------------------ | ---- | ------------ |
| (a) | Crude protein                        | min. | 22           |
|     | Methionine                           | min. | 0.45         |
|     | Total sugar                          | max. | 12           |
|     | Calcium                              |      | 0.7 to 1.2   |
|     | Phosphorus                           | min. | 0.6          |
|     | Sodium                               |      | 0.12 to 0.3  |
| (b) | Manganese                            | min. | 50 mg        |
|     | Zinc                                 | min. | 50 mg        |
|     | Vitamin A                            | min. | 6 000 IU     |
|     | Vitamin $D_3$                        | min. | 750 IU       |
|     | Riboflavin (Vitamin $B_2$)           | min. | 4 mg         |
|     | Vitamin $B_{12}$                     | min. | 10 μg        |
| (c) | 2-(2,6-Dichloroanilino)-2-imidazoline | | 0.08–80 ppm |

EXAMPLE 5

Sole fodder for fattening lambs

| (a) | Crude protein | min. | 16 |
| --- | --- | --- | --- |
| | Crude fibre | max. | 8 |
| | Crude ash | max. | 9 |
| | Calcium | min. | 1 |
| | Phosphorus | min. | 0.5 |
| | (Ca:P ratio not less than 2:1) | | |
| (b) | Vitamin A | min. | 10 000 IU |
| | Vitamin D | min. | 1 250 IU |
| | Vitamin E | min. | 12 mg |
| (c) | 2-(2,6-Dichloroanilino)-2-imidazoline 0.02–200 ppm | | |

EXAMPLE 6

Sole fodder for fattening turkeys

| (a) | Crude protein | min. | 14 |
| --- | --- | --- | --- |
| | Methionine based on Crude protein | min. | 2 |
| | Total sugar | max. | 12 |
| | Calcium | | 0.7 to 1.7 |
| | Phosphorus | min. | 0.7 |
| | Sodium | | 0.12 to 0.3 |
| (b) | Manganese | min. | 50 mg |
| | Zinc | min. | 50 mg |
| | Vitamin A | min. | 8 000 IU |
| | Vitamin D$_3$ | min. | 1 000 IU |
| | Riboflavin (Vitamin B$_2$) | min. | 4 mg |
| | Biotin | min. | 0.15 mg |
| (c) | 2-(2,6-Dichloroanilino)-2-imidazoline 0.08–80 ppm | | |

What is claimed is:

1. A method for promoting growth in an animal which comprises administering to said animal a growth promoting amount of an imidazoline of the formula

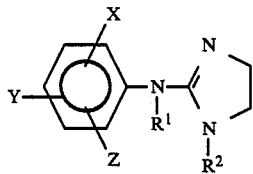

wherein $R^1$ is hydrogen or alkyl;
$R^2$ is hydrogen, benzoyl or acetonyl;
Y is hydrogen, a halogen atom, alkyl, haloalkyl, alkoxy, haloalkoxy, amino, nitro, hydroxy, alkylthio, halothio, or cyclopropyl; and,
X and Z are the same or different and each is hydrogen, a halogen atom, alkyl, haloalkyl, alkoxy, haloalkoxy, amino, nitro, hydroxy, alkylthio, or halothio; or,
X or Z together form —(CH$_2$)$_4$—,
or a physiologically acceptable acid addition salt thereof.

2. A method for promoting growth in an animal which comprises administering to said animal a growth promoting amount of a compound selected from the group consisting of:
2-[1-(2,6-dichlorophenoxy)ethyl]-2-imidazoline,
2-(4-t-butyl-2,6-dimethyl-3-hydroxy-benzyl)-2-imidazoline,
2-(4-t-butyl-2,6-dimethyl-benzyl)-2-imidazoline,
2-(1,2,3,4-tetrahydro-1-naphthyl)-2-imidazoline
2-(1'-naphthylmethyl)-2-imidazoline,
2-[N-(4-hydroxy-2-methylbenzylidene)hydrazino]-2-imidazoline, and
2[O-cyclopropylphenoxy)methyl]-2-imidazoline, and the physiologically acceptable acid addition salts thereof.

3. In accordance with claim 1, the method wherein the imidazoline is selected from the group consisting of:
2-(2,6-dichloroanilino)-2-imidazoline,
1-acetonyl-2(2,6-dichlorophenylamino))-2-imidazoline,
2-(2-bromo-6-fluoroanilino)-2-imidazoline,
2-(2-fluoro-6-trifluoromethylphenylamino)-2-imidazoline,
2-(2-chloro-5-trifluoromethylphenylamino)-2-imidazoline,
2-(2-chloro-4-cyclopropylphenylamino)-2-imidazoline,
2-(3-fluoro-4-methylphenylamino)-2-imidazoline,
1-benzoyl-2-(2,6-dichloroanilino)-2-imidazoline,
2-(1,2,3,4-tetrahydro-5-naphthylamino)-2-imidazoline,
2-(4-amino-2,6-dichlorophenylamino)-2-imidazoline,
2-(3,4-dihydroxy-phenylamino)-2-imidazoline, and the physiologically acceptable acid addition salts thereof.

* * * * *